United States Patent [19]

Klein et al.

[11] 4,095,904
[45] Jun. 20, 1978

[54] DEVICE FOR OBJECTIVE CHECKING FOR FOREIGN BODIES IN OPTICALLY TRANSPARENT CYLINDRICAL CONTAINERS FILLED WITH LIQUIDS

[75] Inventors: Hans Joachim Klein, Wuppertal; Fritz Henze, Leverkusen, both of Germany; Bernhard Vinzelberg, deceased, late of Leverkusen, Germany, by Selma Margot Vinzelberg, Peter Vinzelberg, heirs; by Susanne Klein nee Vinzelberg, heir, Remscheid, Germany

[73] Assignee: Bayer Aktiengesellschaft, Leverkusen, Germany

[21] Appl. No.: 687,845

[22] Filed: May 19, 1976

[30] Foreign Application Priority Data

Jun. 11, 1975 Germany .............................. 2525912

[51] Int. Cl.² .......................................... G01N 21/24
[52] U.S. Cl. ...................................... 356/197; 250/576
[58] Field of Search ................. 356/197; 250/573, 576

[56] References Cited

U.S. PATENT DOCUMENTS

| 2,791,696 | 5/1957 | Schell | 356/197 |
| 3,415,997 | 12/1968 | Vinzelberg et al. | 356/197 |
| 3,942,897 | 3/1976 | Takahashi et al. | 356/197 |
| 3,966,332 | 6/1976 | Knapp et al. | 356/197 |

Primary Examiner—Vincent P. McGraw
Attorney, Agent, or Firm—Burgess, Dinklage & Sprung

[57] ABSTRACT

The device is based on an optical transmission arrangement in which a signal change occurs when a foreign body is present in the liquid. By means of a rotating device the cylindrical container to be tested is set in rotation and subsequently braked. Then optical testing is carried out. The light beams passing through the container are picked up by a plurality of photo electric detectors arranged above one another. The photodetectors are divided into groups, which are each switched on sequentially be a programme control unit from top to bottom to effect the measurement, with one photodector group being switched on when the vortex of liquid occurring as a result of the container rotation has subsided after the standstill of the container and disappeared from the field of view of the photodector group.

8 Claims, 5 Drawing Figures

DEVICE FOR OBJECTIVE CHECKING FOR FOREIGN BODIES IN OPTICALLY TRANSPARENT CYLINDRICAL CONTAINERS FILLED WITH LIQUIDS

The present invention relates to an apparatus and a method for monitoring for foreign bodies in optically transparent containers containing liquids.

In containers such as bottles and ampoules containing liquids, it often happens that undesirable foreign bodies, such as sludge, glass splinters, dirt or precipitate from the liquid are present in the liquid. The checking of each individual container and the subsequent sorting out of the defective containers, i.e. those containing foreign bodies, is necessary.

The invention therefore relates to a device for the automatic and objective checking for foreign bodies in optically transparent cylindrical containers filled with liquids, in particular filled pharmaceutical ampoules. The device comprises a transmitted light beam path with a photoelectric receiver as the detector, at which a signal change occurs when a foreign body is present in the liquid. A rotating device ensures that the cylindrical container is set in rotation before the check and is subsequently braked, so that after the container has come to a stand-still the liquid in the container executes a decreasing rotation movement. In this way any foreign bodies present in the liquid are swirled around.

In the known methods of this kind the foreign bodies moving in the still rotating liquid after the rotation of the ampoule and the subsequent stopping of the ampoule are detected by their effecting a change in the intensity of the light transmitted by the liquid onto a single photoelectric receiver (U.S. Pat. No. 2,253,581, U.S. Pat. No. 2,635,194, German Pat. No. 1,227,254) or of the light dispersed onto the particles and thus deflected from the actual beam path (e.g. German Auslegesschrift No. 1,135,680, German Pat. No. 1,141,471). This method has the following essential disadvantage: in order to cause the foreign bodies in the ampoule to swirl up, the ampoule must be set in violent rotation. In so doing a turbulence is formed which reaches down to the bottom of the ampoule. After the ampoule has been stopped it is then necessary to delay the measurements until the turbulence in the liquid has subsided to such an extent that it has disappeared from the measurement beam path. During this not negligibly small time it can happen that the previously swirled-up foreign body returns to the bottom of the ampoule even before the measurement has begun and thus the measurement is no longer obtainable. In this way, frequently particularly unpleasant foreign bodies such as large glass splinters are not detected.

The object of the invention therefore is to improve the monitoring of the ampoule for impurities in the liquid to such an extent that the above disadvantages are eliminated and also that foreign bodies are detected which by virtue of their size and/or their weight or because of the starting conditions present in the rotation of the ampoule only move for an excessively short time in the still rotating liquid after the ampoule comes to a halt.

According to the invention, there is provided an apparatus for monitoring for foreign bodies in an optically transparent container containing a liquid, comprising means for producing a beam of light passing through the container, a device for rotating the container and subsequently braking it, a plurality of photodetectors arranged one above another, the photodetectors being divided into groups which, in use, are switched on for measurement sequentially from top to bottom by a programme control unit, and a lens which, in use, focusses the light passing through the liquid onto the photodetectors.

There is also provided a method for monitoring for foreign bodies in a optically transparent container containing a liquid, wherein the container is set in rotation and then braked, a beam of light is passed through the container and focussed onto a plurality of photodetectors arranged one above another, and groups of photodetectors are switched on for measurement sequentially from top to bottom as the vortex in the liquid occurring as a result of the rotation of the container has subsided and has disappeared from the field of view of the respective group of photodetectors. The term "group of photodetectors", as used herein, is intended to include one or more photodetectors.

The lens thus reflects the lower half of the liquid column in the container onto the upper group of photodetectors and the upper half onto the lower group of photodetectors. The detection of foreign bodies relies on the foreign bodies carried along in the rotating liquid in the upper and lower halves of the liquid effecting a change in the light intensity recorded at the lower and upper photodetectors.

A refinement of the invention provides that only those photodetectors are switched on which are struck by the light passing through the liquid column. In this way interference effects caused by the surface of the liquid are eliminated. The appropriate coordinated switching of a certain number of photodetectors permits containers of the same size but with differing quantities of liquid to be monitored in the same measurement apparatus easily by the simple electrical switchover of the photodetectors.

The simplest embodiment of the invention is that the photodetectors are divided into two groups and each group consists of a single photodetector. With this embodiment, in each monitoring process, after the container has been rotated and subsequently stopped, firstly the upper photodetector is switched on at the moment when the liquid turbulence subsiding has disappeared from the field of view of the photodetector. The switching on of the lower photodetector takes place in a similar manner at a later moment, namely when the liquid turbulence has disappeared from its measurement beam path.

The use of at least two photodetectors in one arrangement presupposes the same sensitivity in each measurement channel of the arrangement in order to obtain useable measurement results. This is achieved by assigning to each photodetector a measurement channel with its own alternating voltage amplifier and by making the light source powered with direct voltage modulatable by the superimposition of an alternating voltage, so that the same modulated light signal can be supplied to all the photodetectors and the alternating voltage amplifiers can be standardised to the same output signal.

The advantages of the invention are based on the fact that the measurement process begins at an earlier point than if only a single detector were used. The effect of this is that the foreign bodies which are otherwise not accessible to measurement after swirling-up because of a premature sinking to the bottom of the ampoule, can now be detected. The new apparatus thus offers greater certainty in the detection of relatively large, fast-sinking foreign bodies.

A further advantage is that the apparatus can be used without modification for checking ampoules with varying contents. By a simple switch-over process, only those photodetectors which are struck by the light passing through the ampoule liquid are used as detectors. With the hitherto known ampoule testing devices a high degree of work was required if ampoules of one and the same type but having differing liquid contents were to be measured. To achieve this the whole apparatus had to be refitted.

The construction and method of working of the invention are further illustrated for one embodiment with reference to the accompanying drawings.

Figure 1:
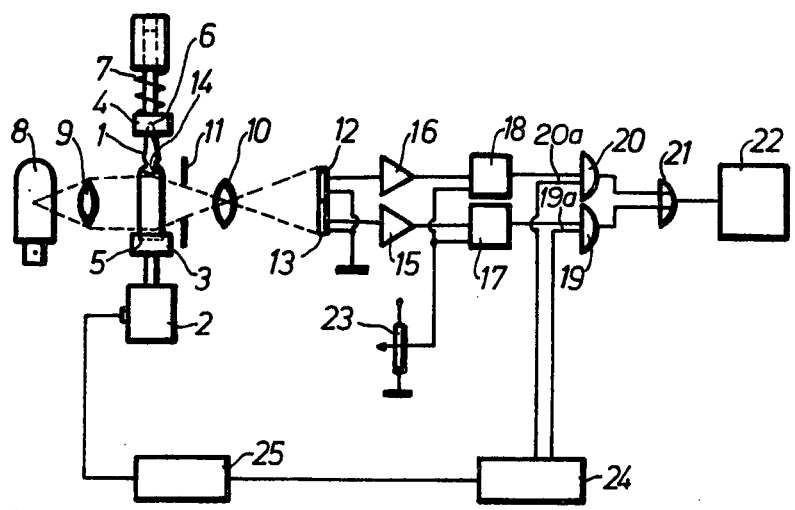
FIG. 1 shows a schematic arrangement of an ampoule testing unit.

FIG. 1 shows a schematic illustration of an embodiment of the ampoule testing unit. The ampoule 1 is located during measurement in a rotating device, comprising a drive motor 2, a rotating plate 3 and a support 4 in the lowered state. For reasons of centring, the ampoule is introduced into a depression 5 in the rotating plate 3 approximately the thickness of the ampoule bottom and into a depression 6 adapted to engage the ampoule point in the support 4. The support 4 is pressed by a spring 7 onto the ampoule, to ensure that the ampoule sits firmly during rotation. For the purposes of introducing and removing the ampoule, the support 4 can be lifted for example by a lifting or rotating magnet.

By means of the lamp 8 and the lens 9 working as a condenser, parallel beams of light pass through the ampoule 1 and by means of the lens 10 through a shutter 11 arranged as a beam limiter onto the two photodetectors 12 and 13, which in this case are arranged directly above one another and are of equal size. A light or image conducting optical system can also be used for the optical system (glass fiber optics). Suitable photodetectors include large surface photo-diodes, photo-transistors, photo-resistances etc.

Figure 2:
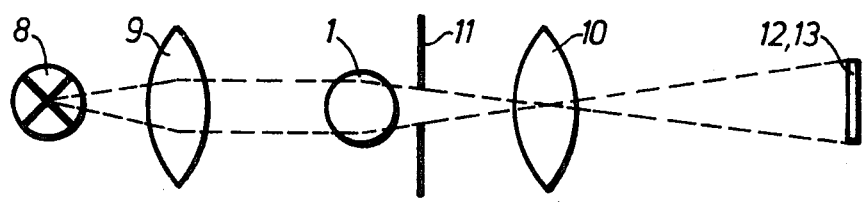
FIG. 2 shows a plan view of the beam path of the arrangement of FIG. 1.

FIG. 2 shows a plan view of the beam path. The shutter 11 arranged directly behind the ampoule limits the beam path through the ampoule liquid at the bottom to immediately above the rotating plate 3 and at the top up to a point immediately below the surface 14 of the ampoule liquid, so that only the part of the ampoule liquid which is to be measured is reflected onto the photodetectors 12 and 13. This takes place symmetrically, so that the lower half of the liquid is reflected onto the upper receiver 12 and the upper half of the liquid is reflected onto the lower receiver 13. In order to minimise the disruptive effect of the ampoule filled with liquid as an effective cylindrical lens, the beam path is limited by means of the shutter 11 to a narrow parallel middle zone symmetrical to the ampoule axis (FIG. 2). The shutter 11 could of course be incorporated at another point in the beam path with the same effect e.g. before the photodetectors 12 and 13, or it can be omitted, if the two detectors are used at the same time as beam limiters in the above sense.

Figure 3:
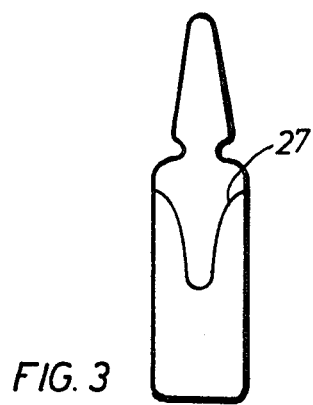
FIG. 3 shows an ampoule with rotating liquid at a specific point in time.

To the photodetectors 12 and 13 there are connected amplifiers 15 and 16, with discriminators 17 and 18 for example in the form of Schmitt triggers being connected to the amplifiers to suppress a certain noise level and to the discriminators there are connected the and-gates 19 and 20, whose outputs are brought together by the or-gate 21. 22 in this case is a circuit which is not described in more detail for storing and/or rejecting ampoules recognised as being defective. The elements 12, 16, 18 and 20 thus constitute the measurement channel for the lower ampoule half and the elements 13, 15, 17 and 19 constitute the measurement channel for the upper ampoule half. The division of the ampoule liquid into two areas of equal size is arbitrary and can be replaced by any other means of division. With a potentiometer 23 connected to a stable positive voltage, a common adjustable threshold value voltage is supplied to the discriminators 17, 18, with which the sensitivity of the arrangement is determined. 24 is a known programme control unit with which the ampoule measurement is determined in respect of time. This takes place as follows: first the motor 2 and thus the ampoule 1 are set in rapid rotation by the motor control 25. The ampoule rotates at approximately 4000 rpm. Then it is suddenly braked, while the ampoule liquid and any foreign bodies present in it continue to rotate for a period. For the motor it is preferable to use a disc armature motor (ferrite type print motor), driven via a suitable power amplifier. Thus it is possible to set the ampoule in rotation in a short time and suddenly to brake it. A vortex is formed in the liquid by the rotation of the ampoule reaching to the bottom of the ampoule which is still present after the ampoule stops, which continues to rotate and which makes measurement at this point impossible. During this time the and-gates 19 and 20 are blocked through the imputs 19a and 20a. Thus it is necessary to wait until the vortex has receded sufficiently so that firstly it has disappeared from the lower half of the ampoule liquid, so that it no longer causes any interference on the photodetector 12. This condition of the vortex 27 is illustrated in FIG. 3. At this point, the and-gate 20 through the input 20a is opened by the programme control unit 24, so that any moving foreign bodies present in the lower half of the ampoule trigger off electrical defect impulses at the photodetector 12, which are amplified in the amplifier 16 and insofar as they exceed the threshold value tension adjusted at the potentiometer 23, they pass through the opened and-gate 20 and the or-gate 21 to the circuit 22, which effects the storage and/or the rejection of the ampoule. If the vortex has receded to such an extent that it no longer interferes with measurement with the photodetector 13, the and-gate 19 is also opened by the programme control unit 24 through the input 19a, so that then the monitoring of the upper half of the ampoule for foreign bodies which might be contained in it can take place via the measurement channel consisting of the elements 13, 15, 17 and 19 in a corresponding manner. After a time determined by the programme control circuit 24, monitoring is terminated by closing the gates 19 and 20 and the ampoule if it was defective is stored by the circuit 22 as defective and/or after transport from the test unit is sorted into a rejection unit. The determination of the individual times in the programme control circuit 24 should be effected according to the ampoule, since it depends on the size of the ampoule and the liquid contained in it. However experience has shown that as a rule a universal adjustment relative to the specific ampoule size and contents, e.g. 2 ml ampoules, regardless of the type of ampoule liquid, is sufficient.

The above described arrangement with the sub-division of the ampoule into a lower and upper half makes it possible also to find such foreign bodies as coarse glass splinters etc. by the early, interference-free switching on of the measurement channel for the lower half, which because of their size or weight would already be lying on the bottom of the ampoule again at the beginning of the measurement, if a total of only one measurement channel were switched on for the ampoule after the recession of the vortex.

The division chosen for the embodiment into two zones of equal size is arbitrary. Naturally for better adaptation to the measurement process, the ampoule can be divided into a plurality of zones, optionally of differing sizes, with a corresponding number of photodetectors arranged above one another, which can also be of different sizes, which are then successively activated from top to bottom according to the measurements. Sub-division into a plurality of zones using several photodetectors arranged immediately above one another also offers the advantage of measuring ampoules of the same size with differing liquid quantities in the same measurement unit by means of simple electronic switching with simultaneous sub-division of the measurement zone.

Figure 4:
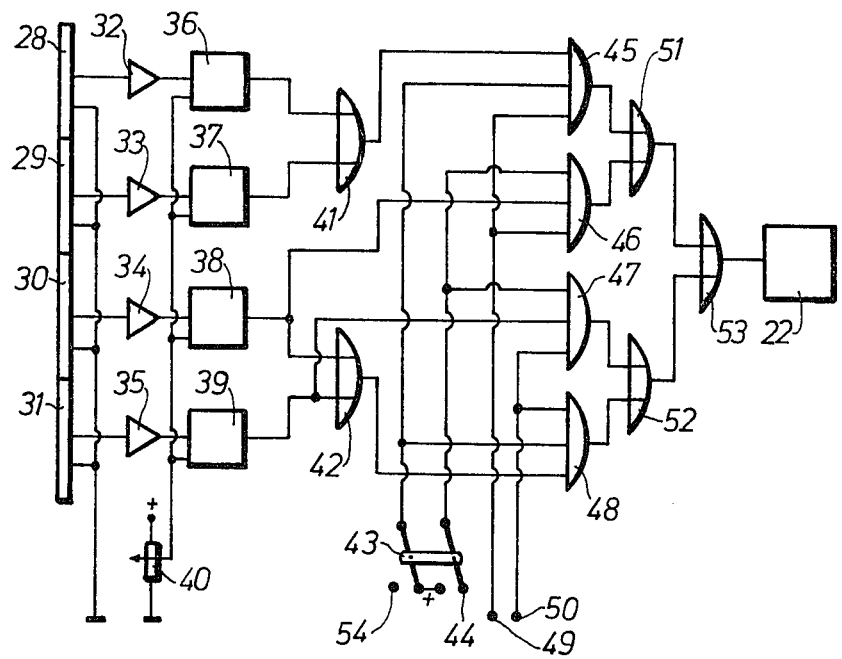
FIG. 4 shows a photodetector and switching arrangement for the measurement of ampoules of the same size with differing liquid quantities.

FIG. 4 shows such a circuit for four photodetectors, with which an ampoule with a specific quantity of liquid, divided into a lower and an upper half, can be tested, but with which it is also possible to measure an ampoule of the same size with only half the quantity of liquid, also subdivided into a lower and an upper half. The amplifiers 32, 33, 34 and 35 and the discriminators 36, 37, 38 and 39 are correspondingly connected to the photodetectors 28, 29, 30 and 31 arranged directly above one another as described in FIG. 1 for two detectors. A common threshold value voltage is supplied to the discriminators with a potentiometer 40. The outputs of the discriminators 36 and 37 are joined by an or-gate 41, and those of the discriminators 38 and 39 are joined by an or-gate 42. If the switch 43 is in the position 44, the and-gates 46 and 47 are blocked, since the input through the switch position 44 lies at zero potential. They can therefore be ignored. However the and-gates 45 or 48 are opened by the switch position 44 for the defect impulses coming from the photodetectors 28 and 29 via the or-gate 41 or from the photodetectors 30 and 31 via the or-gate 42, when there is additionally an L-signal at the control inputs 49 and 50. The control inputs 49 and 50 correspond to the inputs 20a and 19a of FIG. 1, with which the measurement of the lower and upper ampoule halves is switched on. Thus in the switch position 44 of the switch 43 the receivers 28 and 29 are switched together via the or-gates 41 and the and-gate 45 for the measurement of the lower ampoule half and the receivers 30 and 31 are switched via the or-gate 42 and the and-gate 48 for the measurement of the upper ampoule half. The and-gates 45 and 48 are joined via the or-gates 51 and 52 and 53, so that the defect impulses finally arrive at the control circuit 22 (cf. FIG. 1), which controls the rejection of the defective ampoules.

If the ampoules to be monitored contains only half the quantity of liquid, then only the photodetectors 30 for the lower half and 31 for the upper half of the quantity of liquid are used by virtue of the switch position 54 of the switch 43. The switch position 54 means that the and-gates 45 and 48 are blocked, so that they together with the receivers 28 and 29 can be ignored, while the and-gates 46 and 47 can now be opened via the control inputs 49 and 50 for the lower or upper half. In this way, the defect impulses of the lower half of the liquid generated at the photodetector 30 pass through the amplifier 34, discriminator 38, and-gate 46 and or-gate 51 and 53 to the circuit 22. Accordingly the defect impulses of the upper half of the liquid generated at the photodetector 31 pass through the switching elements 35, 39, 47, 52 and 53 to the circuit 22.

The embodiment described here with four photodetectors of equal size for the measurement of ampoules with a specific quantity of liquid and half the quantity of liquid, in each case sub-divided into lower and upper halves, can be extended as required. From the circuit it can be seen that by the corresponding alteration and/or extension of the circuit any number of photodetectors, optionally of differing sizes, can be connected together in the desired manner, so that an optimum adaptation to the quantity of liquid to be monitored is possible with any degree of subdivision.

The use in particular of several photodetectors in one arrangement, to obtain perfect measurement results, requires the same sensitivity of each individual measurement channel of the arrangement.

Figure 5:
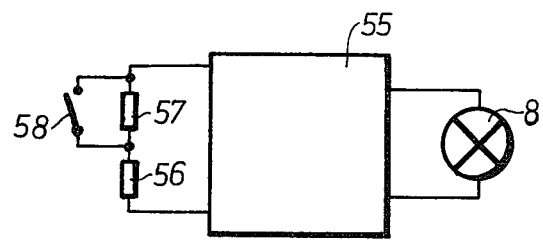
FIG. 5 shows a test circuit for the calibration of the measurement channels.

FIG. 5 shows a circuit diagram with which testing and calibration of the measurement channels can be easily carried out. The lamp 8 for shining light through the ampoules is connected to a programmable direct voltage power supply 55 (e.g. a Valvo PE 1227), whose output direct voltage is determined by the two external resistances 56 and 57 connected in series (1 kOhm/volt output voltage). The relay contact 58, preferably a reed relay, is normally, i.e. during ampoule measurement, open. For testing purposes the relay coil (not shown) of the relay contact 58 is controlled by an impulse generator (not shown), so that the contact 58 opens and closes to the rhythm of the impulse frequency. The resistance 57 is thus bridged at intervals according to the impulses, so that the total resistance with the contact closed is reduced, and the output voltage is therefore also correspondingly lowered. The output voltage connected to the lamp 8 is therefore modulated with a square wave alternating voltage. If in the example given the resistance 56 is 7.7 kOhm and the resistance 57 is 0.3 kOhm, then normally the lamp voltage is 8 volts. If for testing and calibration purposes the contact 58 receives impulses of 62.5 Hz, the modulation on the residual direct voltage of 7.7 volts to a square wave alternating voltage of 300 mV at 62.5 Hz. The modulated lamp voltage results in a modulation of the lamp intensity, so that all the photodetectors are supplied with the same modulated light signal and checking for the same output signals at the amplifier outputs is possible. The modulation of the lamp voltage is of course possible in other ways, e.g. by means of sinusoidal alternating voltages.

What we claim is:

1. An apparatus for monitoring for foreign bodies in an optical transparent container containing a liquid, comprising means for producing a beam of light for passing through the container, a device for rotating the container and subsequently braking the rotating motion, a plurality of photodetectors arranged one above another, an amplifier connected to each of the photodetectors, gate means for switching on the amplifiers to activate the photodetectors in groups successively from top to bottom and a control unit operatively connected to the gate means to enable same to effect activation of the photodetectors in a sequence which is defined by the disappearance of the vortex from the scanning field associated with the respective photodetector group and a lens provided with aperture means for imaging the central portion of the liquid column onto the photodetector array.

2. An apparatus as claimed in claim 1, comprising two groups of photodetectors.

3. An apparatus as claimed in claim 2 wherein each group of photodetectors consists of a single photodetector.

4. An apparatus as claimed in claim 1 wherein each group of photodetectors consists of a single photodetector.

5. An apparatus as claimed in claim 1, wherein the aperture means comprises a shutter for restricting the beam of light.

6. An apparatus as claimed in claim 1, wherein each amplifier comprises an alternating voltage amplifier connected to each photodetector and further comprising means for modulating the light source by superimposing an alternating voltage, whereby all the photodetectors can be supplied by the same modulated light signal and the amplifiers can be standardised to the same output signal.

7. A method for monitoring for foreign bodies in an optically transparent container containing a liquid wherein the container is set in rotation and then braked, a beam of light is passed through the container and focussed through the central portion of the liquid column onto a plurality of photodetectors arranged one above another with an amplifier connected to each, the amplifiers are switched on by gates to activate groups of photodetectors for measurement and the gates are operatively enabled by a control unit to effect activation of the photodetectors sequentially from top to bottom as the vortex in the liquid occurring as a result of the rotation of the container has subsided and has disappeared from the field of view of the respective group of photodetectors.

8. A method as claimed in claim 7, wherein only those photodetectors are switched on which are struck by the light passing through the liquid in the container.

* * * * *